US006615431B2

(12) United States Patent
Lin

(10) Patent No.: US 6,615,431 B2
(45) Date of Patent: Sep. 9, 2003

(54) PORTABLE MASSAGE BED

(75) Inventor: Lawrence Lin, Taiwan (CN)

(73) Assignee: LifeGear, Inc., El Monte, CA (US)

( * ) Notice: Subject to any disclaimer, the term of this patent is extended or adjusted under 35 U.S.C. 154(b) by 0 days.

(21) Appl. No.: 10/002,270

(22) Filed: Nov. 15, 2001

(65) Prior Publication Data

US 2003/0088919 A1 May 15, 2003

(51) Int. Cl.7 .................................................. A61F 5/00

(52) U.S. Cl. .............................. 5/620; 5/600; 606/242; 606/245

(58) Field of Search ........................... 5/620, 618, 617, 5/613, 610, 600; 606/240, 241, 242, 245, 237

(56) References Cited

U.S. PATENT DOCUMENTS

| | | | | | |
|---|---|---|---|---|---|
| 2,517,681 | A | * | 8/1950 | Koerper | 5/620 X |
| 2,579,783 | A | * | 12/1951 | Branto | 5/620 X |
| 3,754,749 | A | * | 8/1973 | Lyon et al. | 5/618 |
| 4,041,786 | A | * | 8/1977 | Offterdinger | 74/29 |
| 4,059,255 | A | * | 11/1977 | Perold | 5/610 |
| 4,103,170 | A | * | 7/1978 | Spradlin | 5/620 X |
| 4,230,100 | A | * | 10/1980 | Moon | 606/242 |
| 4,245,626 | A | * | 1/1981 | Paolino | 606/242 |
| 4,271,830 | A | * | 6/1981 | Moon | 606/244 |
| 4,314,552 | A | * | 2/1982 | Moon | 606/242 |
| 4,582,311 | A | * | 4/1986 | Steffensmeier | 5/614 |
| 4,732,141 | A | * | 3/1988 | Steffensmeier | 606/245 |
| 4,856,497 | A | * | 8/1989 | Westphal | 5/620 X |
| 5,427,436 | A | * | 6/1995 | Lloyd | 297/408 |
| 5,642,542 | A | * | 7/1997 | Kometani | 5/620 |
| D403,772 | S | * | 1/1999 | Fanuzzi | D24/183 |
| 5,954,750 | A | * | 9/1999 | Steffensmeier | 606/237 |
| 6,436,126 | B1 | * | 8/2002 | McAfee | 606/245 |
| 2002/0103504 | A1 | * | 8/2002 | McAfee | 606/240 |
| 2002/0120293 | A1 | * | 8/2002 | Peetros et al. | 606/241 |

* cited by examiner

*Primary Examiner*—Robert G. Santos
(74) *Attorney, Agent, or Firm*—Selitto, Behr & Kim

(57) ABSTRACT

An improved massage bed structure, which is foldable into a compact case to facilitate transport and storage, including a bed frame, a mattress, an inclination adjusting structure and a height adjusting structure. The inclination and height adjusting structures permit easy adjustment of the angles of inclination of a back pad and the massage bed, and the height of a waist and hip pad to comply with ergonomics. A pillow is provided to provide good support for the user's head and is capable of height and angle adjustment. A rest plate is mounted at the lower end of the pillow to provide support for the user's elbows to help the user to relax the shoulder muscles to thereby enhance massaging effects.

2 Claims, 12 Drawing Sheets

PORTABLE MASSAGE BED

BACKGROUND OF THE INVENTION

The invention relates to an improved massage bed structure and, more particularly, to a portable massage bed that permits adjustment of inclination of a mattress, and that is foldable into a compact case to facilitate transport and storage.

Massaging is growing popular because it helps relax body muscles and promote blood circulate. Conventional massage beds are generally provided with some folding mechanism. However, even though some massage beds are foldable, they are still large in size, which is inconvenient to carry around. It would be desirable to have a massage bed that is foldable into a compact size to enable a masseur to carry the massage bed around with relative ease.

SUMMARY OF THE INVENTION

Therefore, an object of the present invention is to provide an improved massage bed structure, more particularly a massage bed that permits easy adjustment of a back pad and the angle of inclination of a waist and hip pad to provide an ergonomic design so that the user can lie comfortably on the bed during a massage and to help the user to relax his/her muscles during the massage to thereby enhance massaging effects. Another object is to provide a massage bed which is foldable into a compact case to facilitate transport and storage.

Accordingly, the massage bed of the invention includes a bed frame, a mattress, an inclination adjusting structure and a height adjusting structure. The bed frame has a mattress disposed thereon. One end of the mattress is provided with a pillow. The bed frame and the mattress are locked relative to each other by means of the inclination adjusting structure and the height adjusting structure.

BRIEF DESCRIPTION OF THE DRAWINGS

The foregoing and other features and advantages of the present invention will be more clearly understood from the following detailed description and the accompanying drawings, in which like elements in different figures thereof are identified by the same reference numeral and wherein.

DETAILED DESCRIPTION

Figure 1:
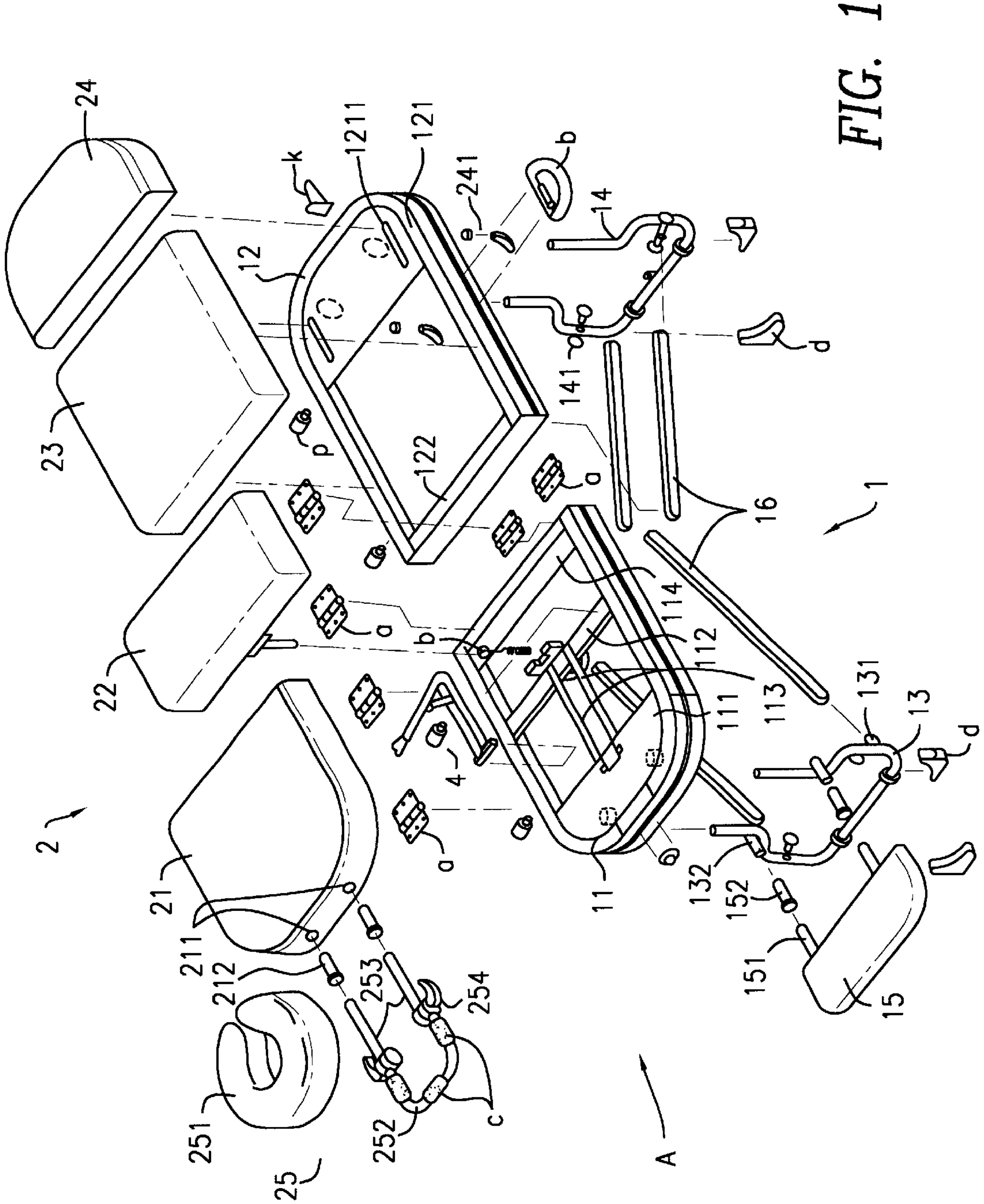
FIG. 1 is an exploded perspective view of the massage bed structure of the invention.
Figure 1A:
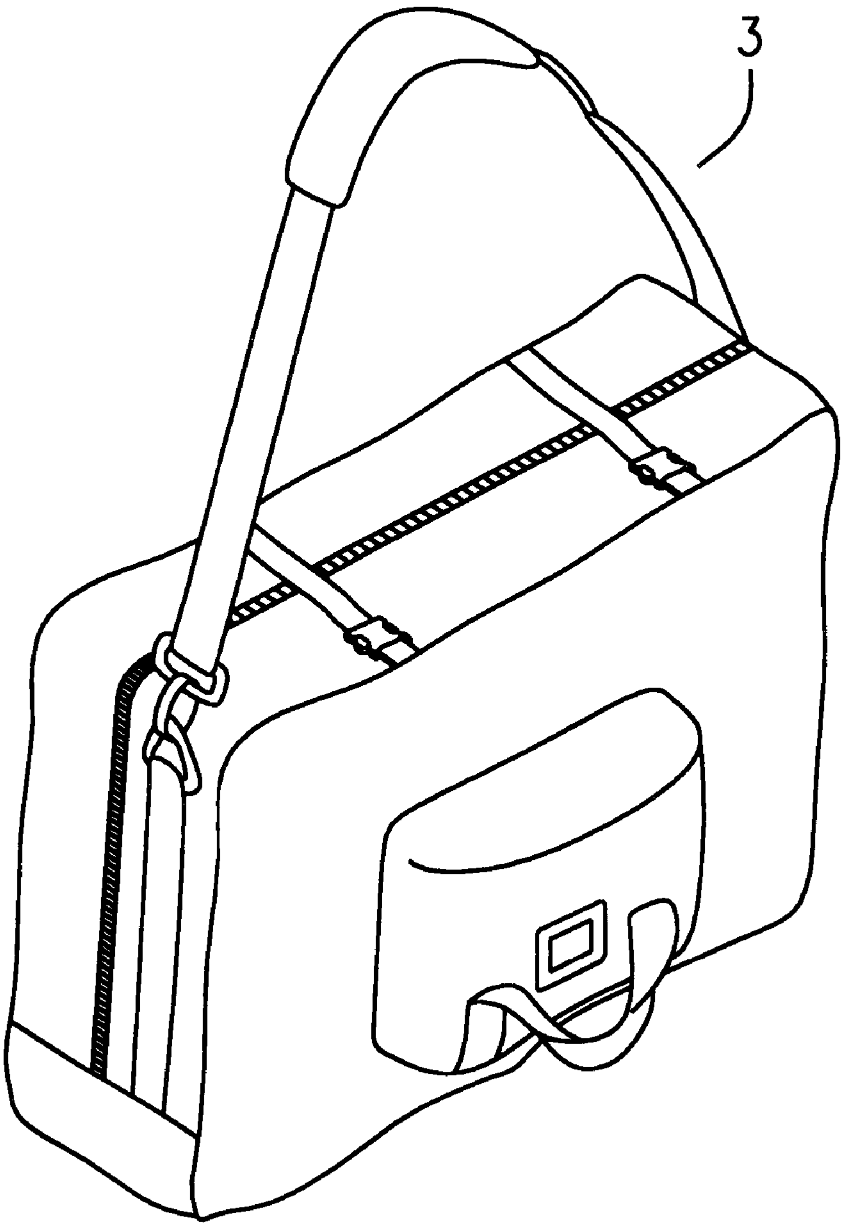
FIG. 1A shows a bag into which the folded bed can be placed for storage and transport.

With reference to FIGS. 1 and 1A, the preferred embodiment of a massage bed A according to the invention includes a bed frame 1 and a mattress 2. A bag 3 is provided to accommodate the folded massage bed A to facilitate carrying and storage. An inclination adjusting structure 4 and a height adjusting structure 5 (FIGS. 4, 8) are provided to lock the bed frame 1 and the mattress 2 relative to each other.

The bed frame 1 includes a first frame 11, a second frame 12, a left leg frame 13, a right leg frame 14, a rest plate 15 and four support rods 16.

The first frame 11 is D-shaped with a hollow portion in which a plate 111 is disposed. The plate 111 has a bottom side with an inverted U-shaped fastener b, and an intermediate section provided with a securing plate 112. The plate 111 and securing plate 112 are mounted relative to each other by connecting links 113. The inner side of a pivotal edge 114 is also provided with an inverted U-shaped fastener b.

The second frame 12 is also D-shaped with a hollow portion in which a plate 121 is disposed. The plate 121 is provided with two parallel grooves 1211 and has a bottom side provided with an inverted U-shaped fastener b. The inner side of a pivotal edge 122 is provided with an inverted U-shaped fastener b.

The left leg frame 13 is substantially T-shaped with left and right sides each provided with a securing pin 131 and an insert tube 132. The bottom portion of the left leg frame 13 is disposed for mounting anti-slip leg sleeves d.

The right leg frame 14 is also substantially T-shaped with left and right sides respectively provided with securing pins 141. The bottom portion of the right leg frame 14 is disposed for mounting anti-slip leg sleeves d.

The rest plate 15 has one side provided with two insert rods 151, each of which has a sleeve 152 fitted thereon.

Each of the support rods 16 has one end disposed on the respective inverted U-shaped fastener b on the pivotal edges 114, 122 of the first and second frames 11, 12, and another end disposed on the respective securing pin 131, 141 of the left and right leg frames 13, 14.

The mattress 2 mainly includes a back pad 21, a waist and hip pad 22, a securing pad 23, a foot pad 24 and a pillow 25. The back pad 21 has one edge provided with two insert holes 211 for insertion of sleeves 212. The foot pad 24 has a bottom portion provided with positioning handles 241.

Figure 2:
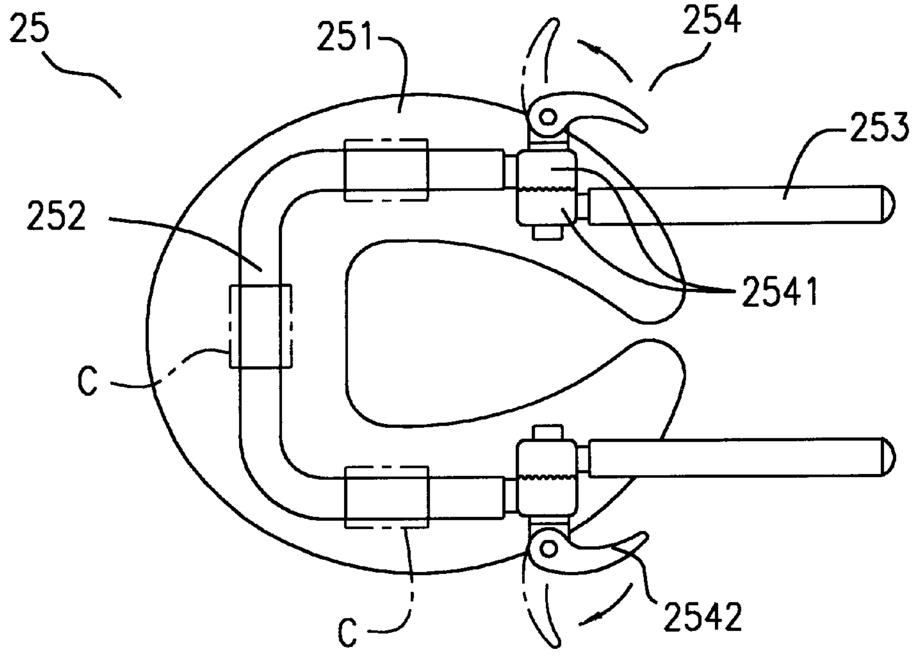
FIG. 2 is a bottom view of the pillow structure of the invention.

Referring to FIG. 2, which is a bottom view of the pillow structure 25 of the invention, a pad 251 within the pillow structure 25 has a central portion formed as a hollow, and a bottom portion provided with hook and loop fasteners c. An adjusting frame 252 is substantially U-shaped and has insert rods 253 at two ends thereof which have intermediate sections each provided with an adjusting assembly 254. The adjusting assemblies 254 are each formed by two indexing blocks 2541 and a handle 2542. The adjusting frame 252 has a bottom portion provided with hook and loop fasteners c.

Figure 3:
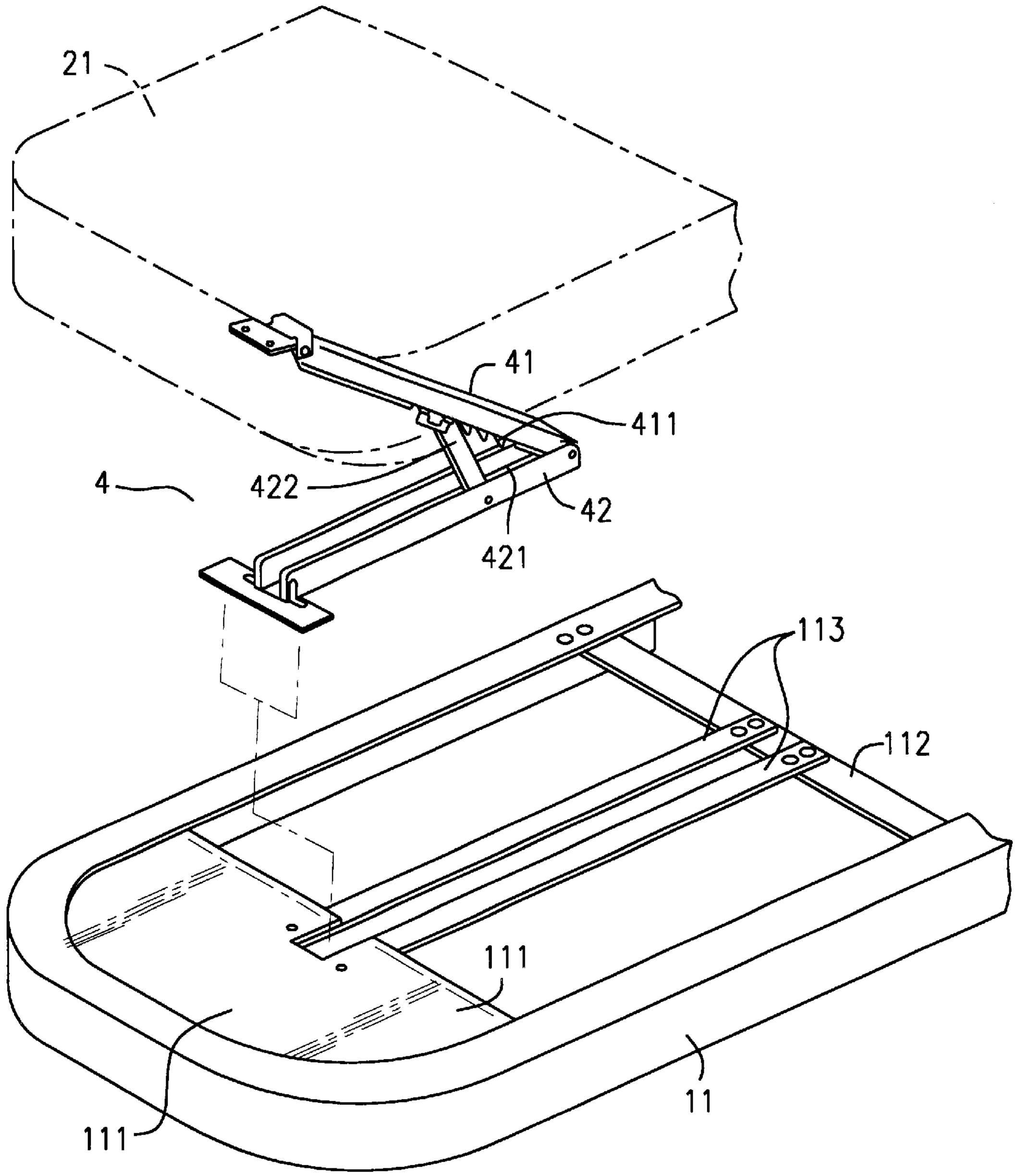
FIG. 3 is an exploded perspective view of the back pad inclination adjusting structure of the invention.

Referring to FIG. 3, the inclination adjusting structure 4 is provided with an upper arm 41 and a lower arm 42. The upper arm 41 has one side provided with toothed grooves 411. The lower arm 42 has a spring 421 disposed therein and is lockably provided with a retaining member 422.

Figure 4:
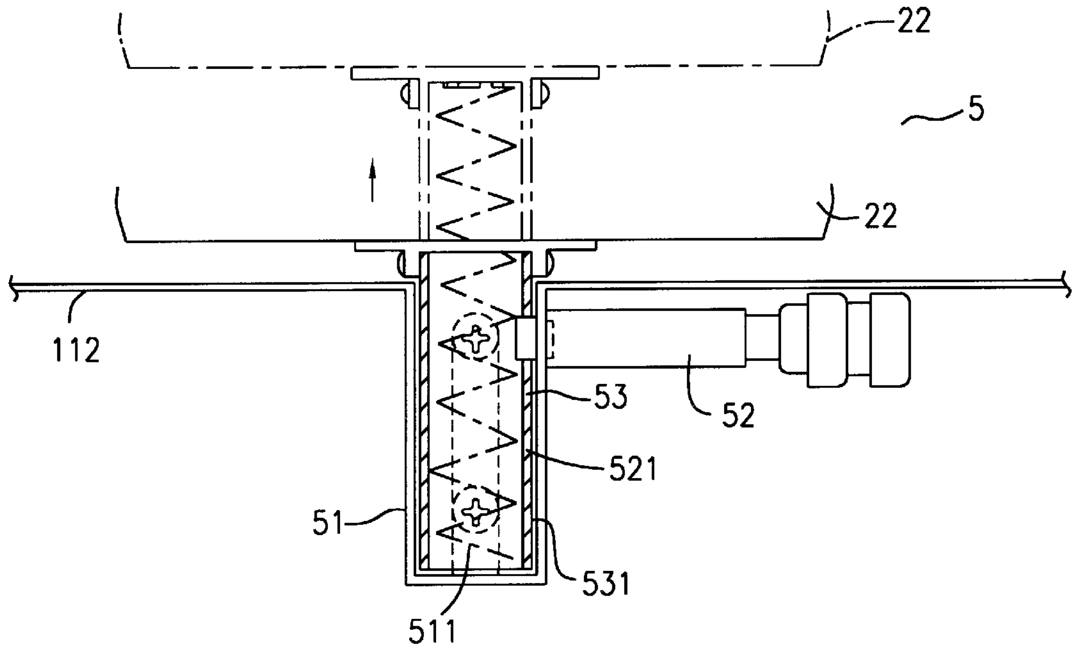
FIG. 4 is a perspective view of the waist and hip height adjusting structure of the invention.

Referring to FIG. 4, the waist and hip height adjusting structure 5 includes a seat 51. The seat 51 has an interior provided with a spring 511, and one side provided with a lock pin 52. A support bar 53 is provided with high and low positioning holes 531 on the side corresponding to the lock pin 52.

During assembly, the pivotal edges 114, 122 of the first and second frames 11, 12 are pivotally connected by hinges, and the inverted U-shaped fasteners b provided on the inner sides of the pivotal edges 114, 122 are pivotally disposed on one end of the support rod 16. The inverted U-shaped fasteners b disposed at the lower ends of the plates 111, 121 of the first and second frames 11, 12 are pivotally connected to the left and right leg frames 13, 14. The other end of the support rod 16 is disposed in the securing pins 131, 141 provided on two sides of the left and right leg frames 13, 14. The bottom portions of the left and right leg frames 13, 14 are provided with anti-slip leg sleeves d to effectively provide an anti-slip function for the massage bed. The sleeves 152 are fitted on the two insert rods 151 of the rest plate 15, and the rest plate 15 is insertably disposed in the insert tubes 132 of the left leg frame 13 to thereby complete assembly of the bed frame 1.

Figure 5:
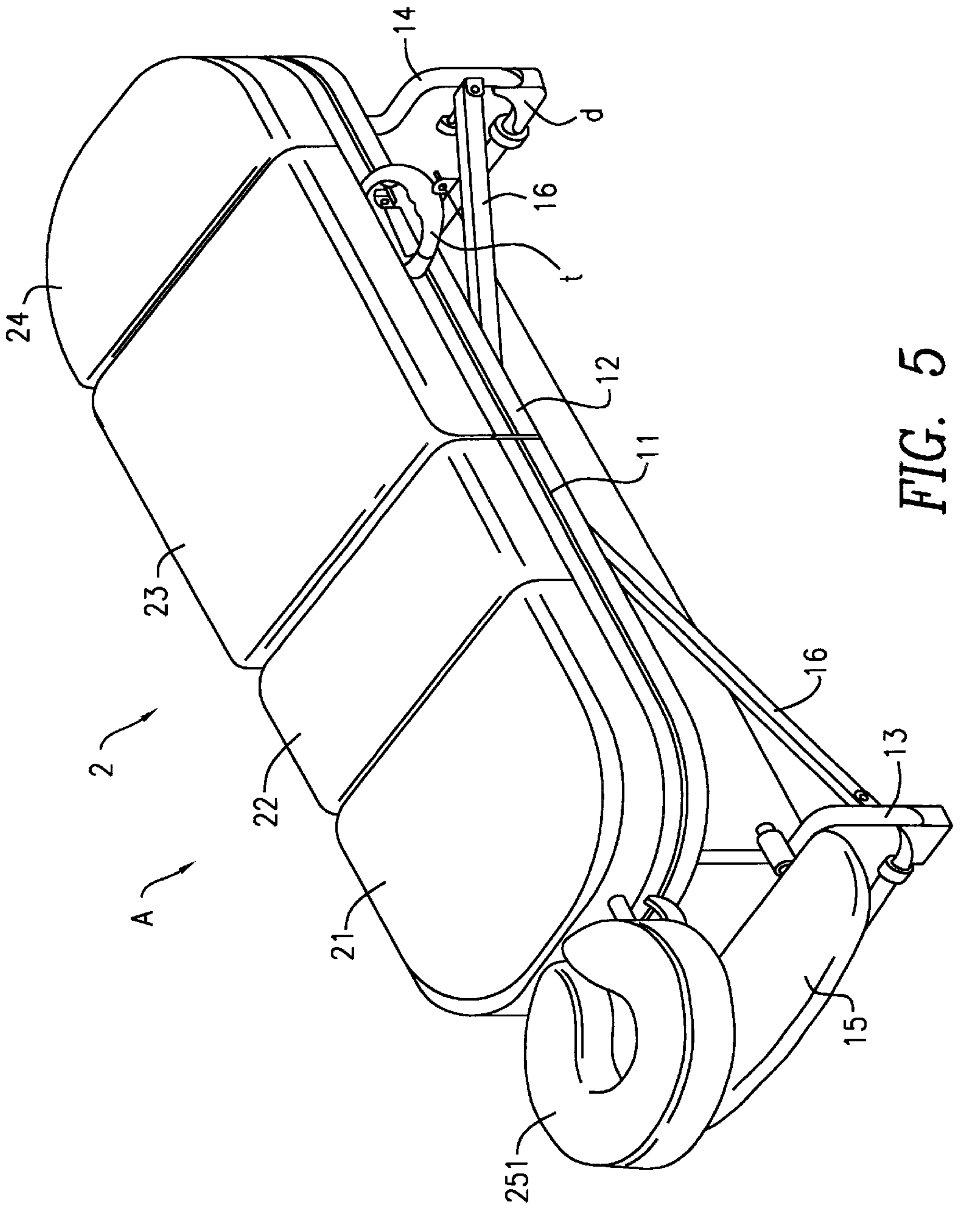
FIG. 5 is an assembled perspective view of the massage bed structure of the invention.

After assembling the bed frame 1, the mattress 2 can be assembled correspondingly onto the bed frame 1. The lower arm 42 of the inclination adjusting structure 4 is correspondingly locked to the plate 111 of the first frame 11, while the upper arm 41 is correspondingly locked to the bottom portion of the back pad 21. The bottom portion of the back pad 21 is provided with hinge a corresponding to the securing plate 112 of the first frame 11 to lock the back pad 21 on the securing plate 112 at a fixed point. One side of the securing plate 111 is provided with the seat 51 of the waist and hip height adjusting structure 5. The interior of the seat 51 has a spring 511 mounted thereon, with a lock pin 52 disposed on one side. The bottom portion of the waist and hip pad 22 is locked together with the support bar 53 of the waist and hip height adjusting structure 5. The support bar 53 extends into the spring 531 in the seat 51. The limiting holes 531 in the support bar 53 are on the same side as the lock pin 52. The lock pin 52 is correspondingly extended into the limiting hole 531 in the support bar 53 to secure the waist and hip pad on the first frame 11. The bottom portion of the waist and hip pad 22 is provided with hinge a corresponding to the pivotal edge 114 of the first frame 11 to lock the waist and hip pad 22 on the pivotal edge 114 at a fixed point. The securing pad 23 and foot pad 24 are correspondingly secured on the second frame 12. The foot pad 24 is locked in the groove 1211 in the plate 121 of the second frame 12 via a positioning handle 241. The insert rods 253 at the two ends of the adjusting frame 252 are insertable into the sleeves 212 in the insert holes 211 of the back pad 21. The rest pad 251 of the pillow 25 and the adjusting frame 252 are provided with matching hook and loop fasteners c to facilitate assembly and detachment (the massage bed thus assembled being shown in FIG. 5).

Figure 6:
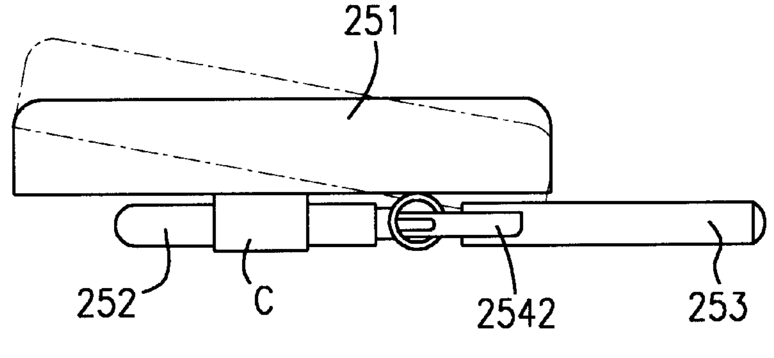
FIG. 6 is a schematic view illustrating operation of the pillow structure of the invention.
Figure 7:
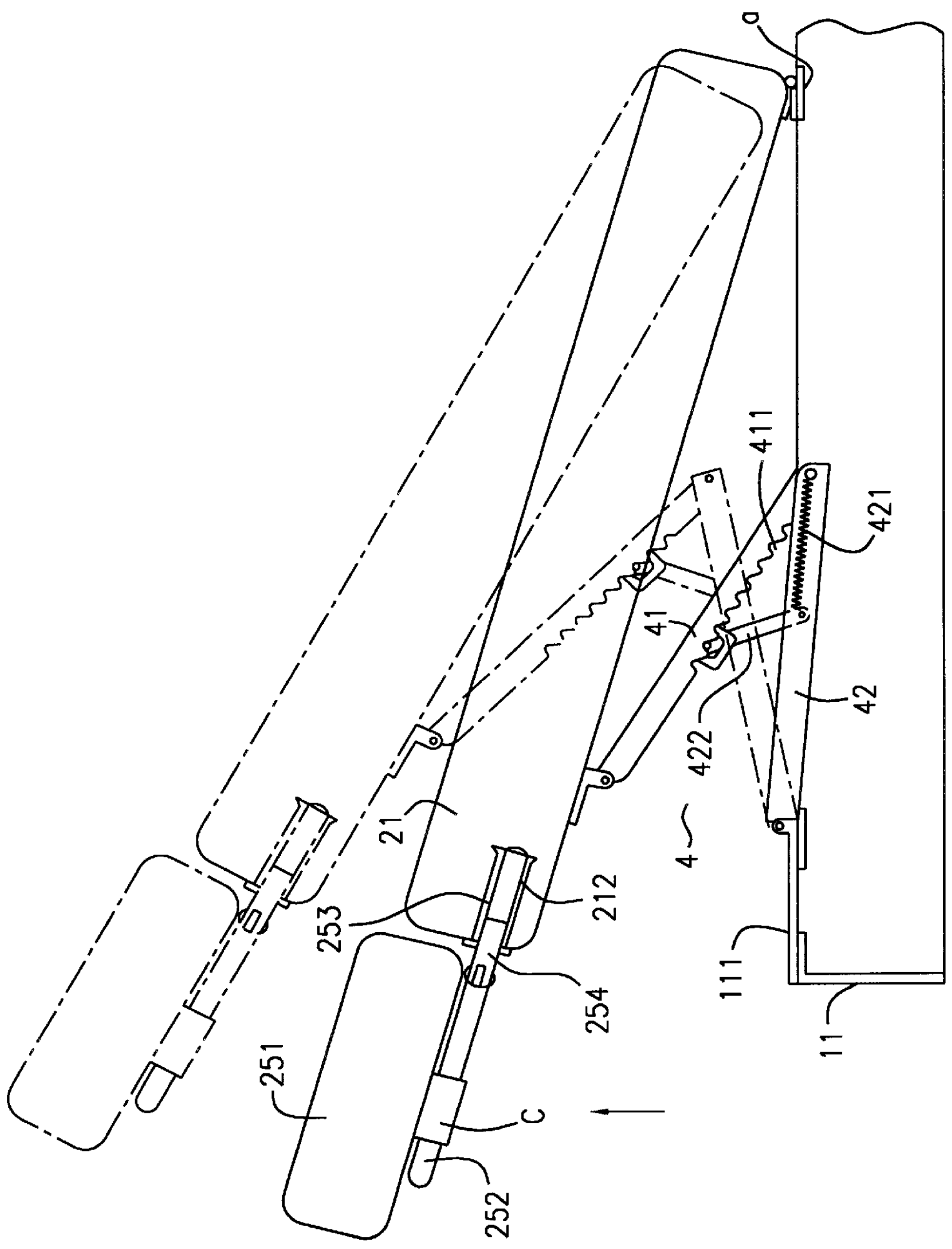
FIG. 7 is a schematic view illustrating operation of the back pad inclination adjusting structure of the invention.

Referring to FIG. 6, which illustrates operation of the present invention, the pillow 25 allows the user to rest his/her head thereon, the adjusting assembly 254 thereof also allows the user to make suitable adjustment so that the user can relax the head muscles to thereby enhance the massaging effect. When the handle 2542 of the adjusting assembly 254 is pulled outwardly (in the direction of the arrow shown in FIG. 2), the indexing blocks 2541 of the adjusting assembly 254 can be released. The user can adjust the inclination of the pillow structure 25 with ease and, after adjustment, turn the handle 2542 of the adjusting assembly 254 in a reverse direction to thereby lock the indexing blocks 2541 of the adjusting assembly 254 tight. Since the mating surfaces of the indexing blocks 2541 are rugged, a good retaining effect can be achieved Referring to FIG. 7, the back pad inclination adjusting structure 4 is disposed between the first frame 11 of the bed frame 1 and the back pad 21 of the mattress 2. When the user wants to adjust the inclination of the back pad 21, it is only necessary to move the back pad 21 upwardly (in the direction of the arrows) to cause the retaining member 422 to slightly disengage from the toothed groove 411 and to adjust the inclination of the back pad 21 at the same time. After adjustment, the retaining member 422 once again engages the toothed groove 411 (after change of inclination of the back pad) for securing purposes. By virtue of the spring 421 that abuts against the retaining member 422, the stability of the structure can be enhanced. As one end of the bed pad 21 is locked to the securing plate 112 of the first frame 11 by hinge a, during inclination adjustment of the back pad 21, the back pad 21 can displace up and down with the hinge a between the back pad 21 and the securing plate 112 of the first frame 11 as center.

Figure 8:
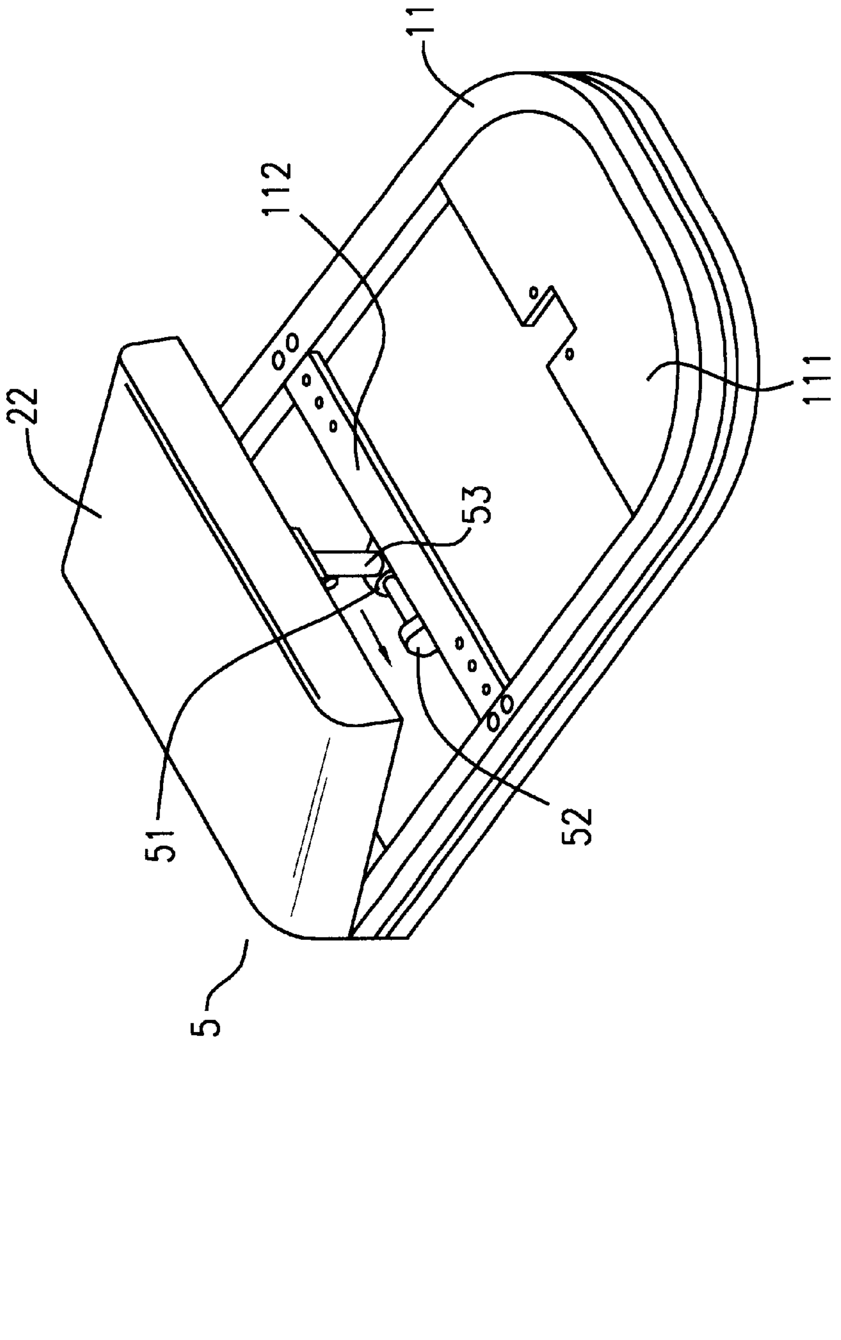
FIG. 8 is a schematic view illustrating operation of the waist and hip height adjusting structure of the invention.

Referring to FIG. 8, which illustrates the operation of the waist and hip height adjusting structure 5, when the user wants to adjust the waist and hip pad 22, the lock pin 52 can be pulled outwardly, so that the distal end of the lock pin 52 moves away from the limiting hole 531 in the supporting bar 53. The user can select one of the high and low limiting holes 531 and thereafter release the lock pin 531 so that the lock pin 531 engages the selected limiting hole 531. As one end of the waist and hip pad 22 is locked to the pivotal edge 114 of the first frame 11 by hinge a, during inclination adjustment of the waist and hip pad 22, the waist and hip pad 22 will displace up and down with the hinge a between the waist and hip pad 22 and the pivotal edge 114 of the first frame 11 as center.

Figure 9:
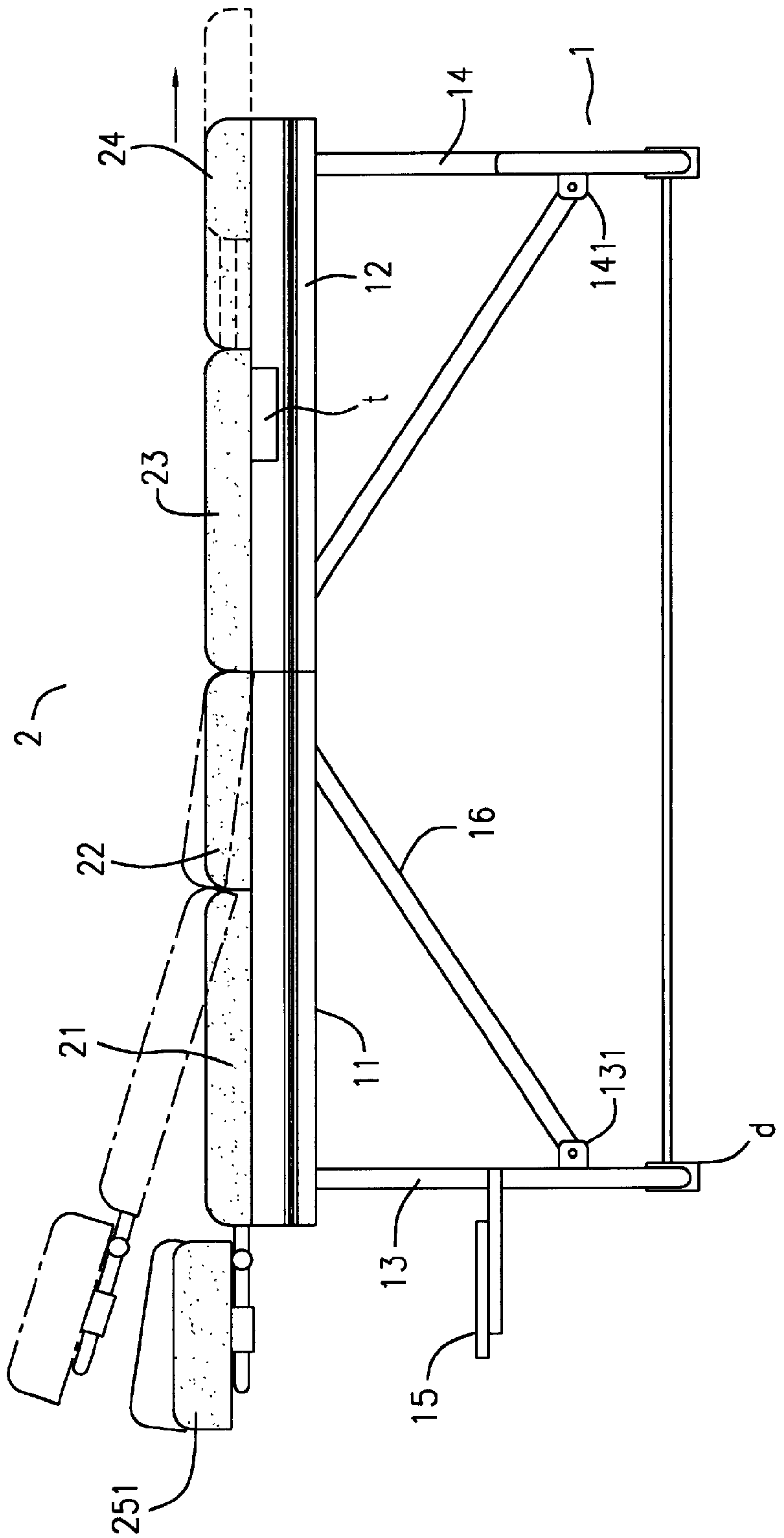
FIG. 9 illustrates displacement of the mattress of the massage bed of the invention.

Referring to FIG. 9, which illustrates displacement of the mattress structure of the invention, the angle of inclination of both the back pad 21 and the waist and hip pad 22 can be adjusted upwardly. The positioning handle 241 at the bottom portion of the foot pad 24 can be released to allow the foot pad 24 to be pulled outwardly to provide flexible adjustment to adapt to users of different heights.

Figure 10:
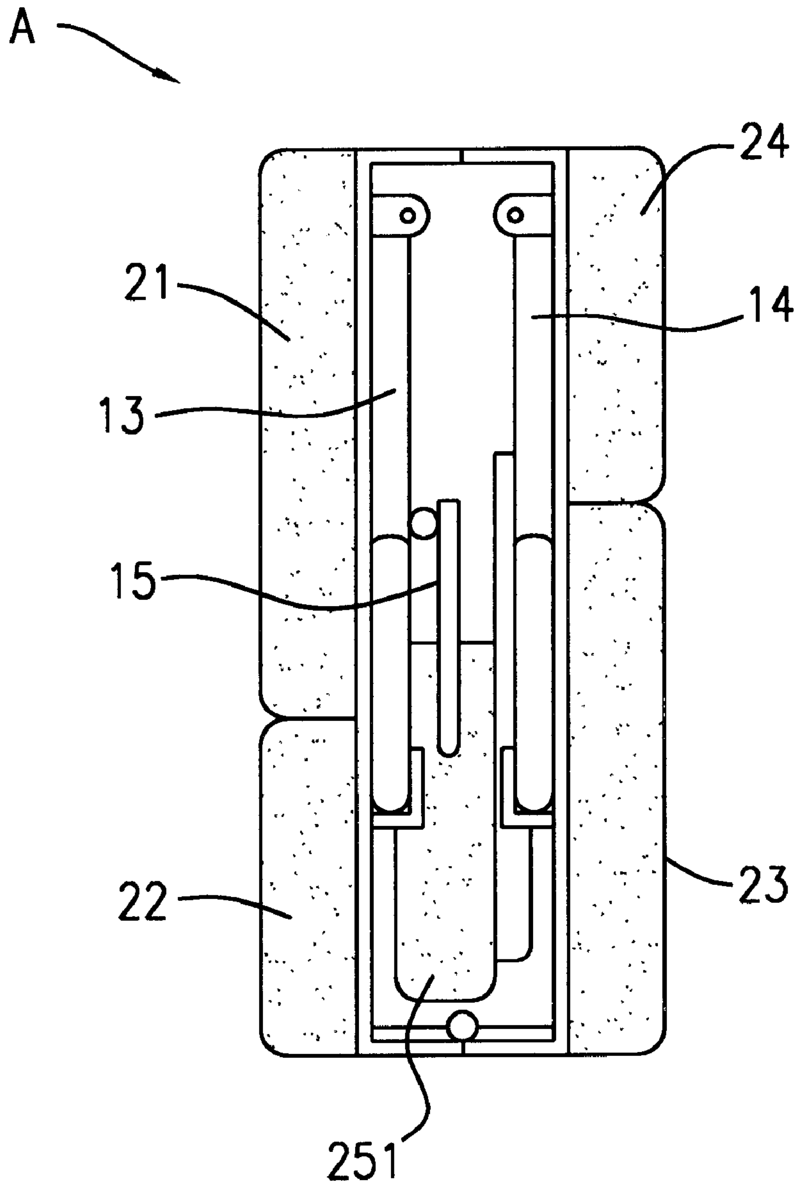
FIG. 10 is a schematic view illustrating the massage bed of the invention in a folded state.
Figure 11:
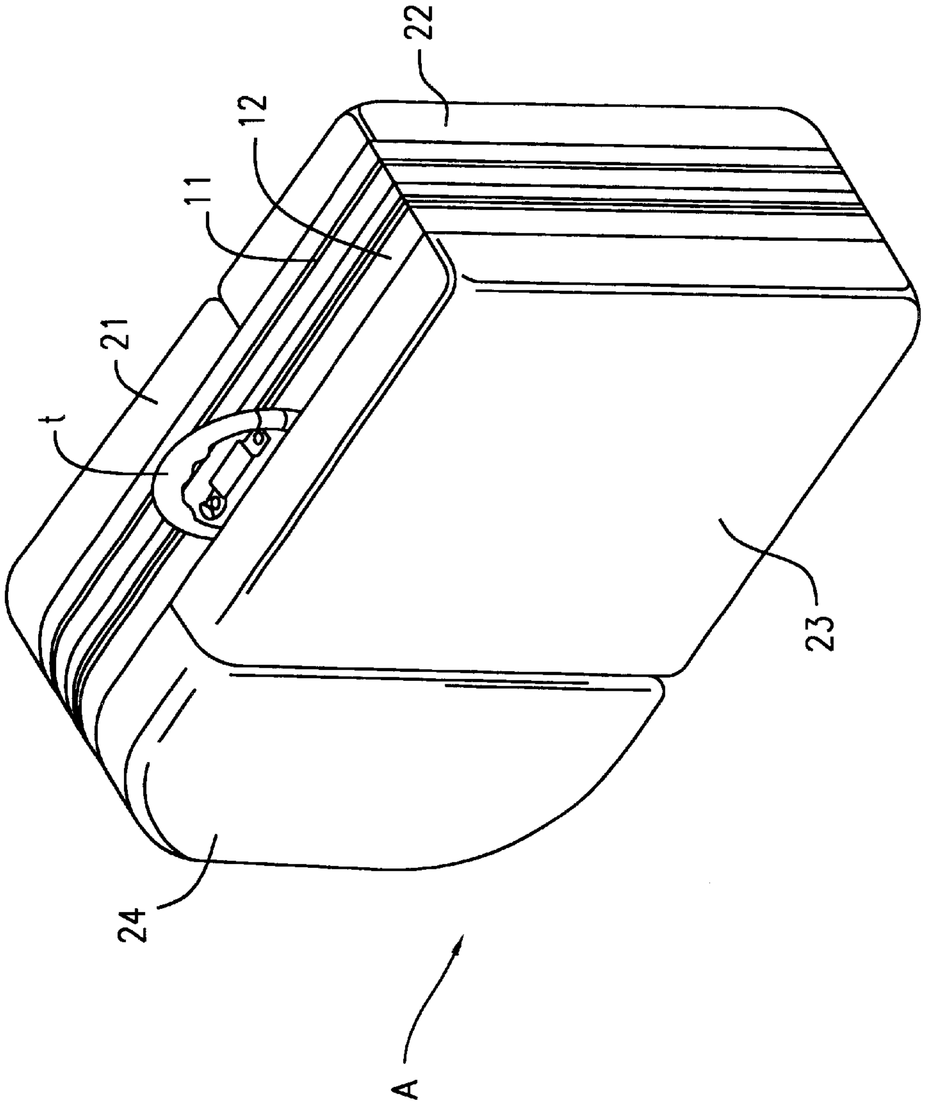
FIG. 11 is a schematic view illustrating the massage bed of the invention in the folded state.

Reference is further made to FIGS. 10 and 11, which illustrates the massage bed in a folded state. The present invention is directed to providing a foldable massage bed A that can be folded into a case to enable a masseur to carry the massage bed A out to attend to senile people or people who are paralyzed after suffering stroke, etc. To fold the massage bed structure A, the massage bed is turned sidewise, with the projection p provided at one side of the second frame 12 of the massage bed A to support the bed body. The securing pins 131, 141 of the left and right leg frames 13, 14 are pulled out to disengage the support rods 16 from the left and right leg frames 13, 14. The support rods 16 are respectively disposed at the bottom portion of the first and second frames 11, 12. The left and right leg frames 13, 14 are bent inwardly. The rest pad 251 of the pillow 25 and the adjusting frame 252 are separated and disposed in the gap between the first and second frames 11, 12. The first and second frames 11, 12 are folded toward each other, with fastening ring k locked. The massage bed A can then be converted into a compact and light case. A handle t is provided on the second frame 12 corresponding to projection p to facilitate carrying.

When travelling, the massage bed A can be taken along in the case form in a very convenient manner. At the destination, the massage bed A can be unfolded for sitting or resting purposes.

Figure 12:
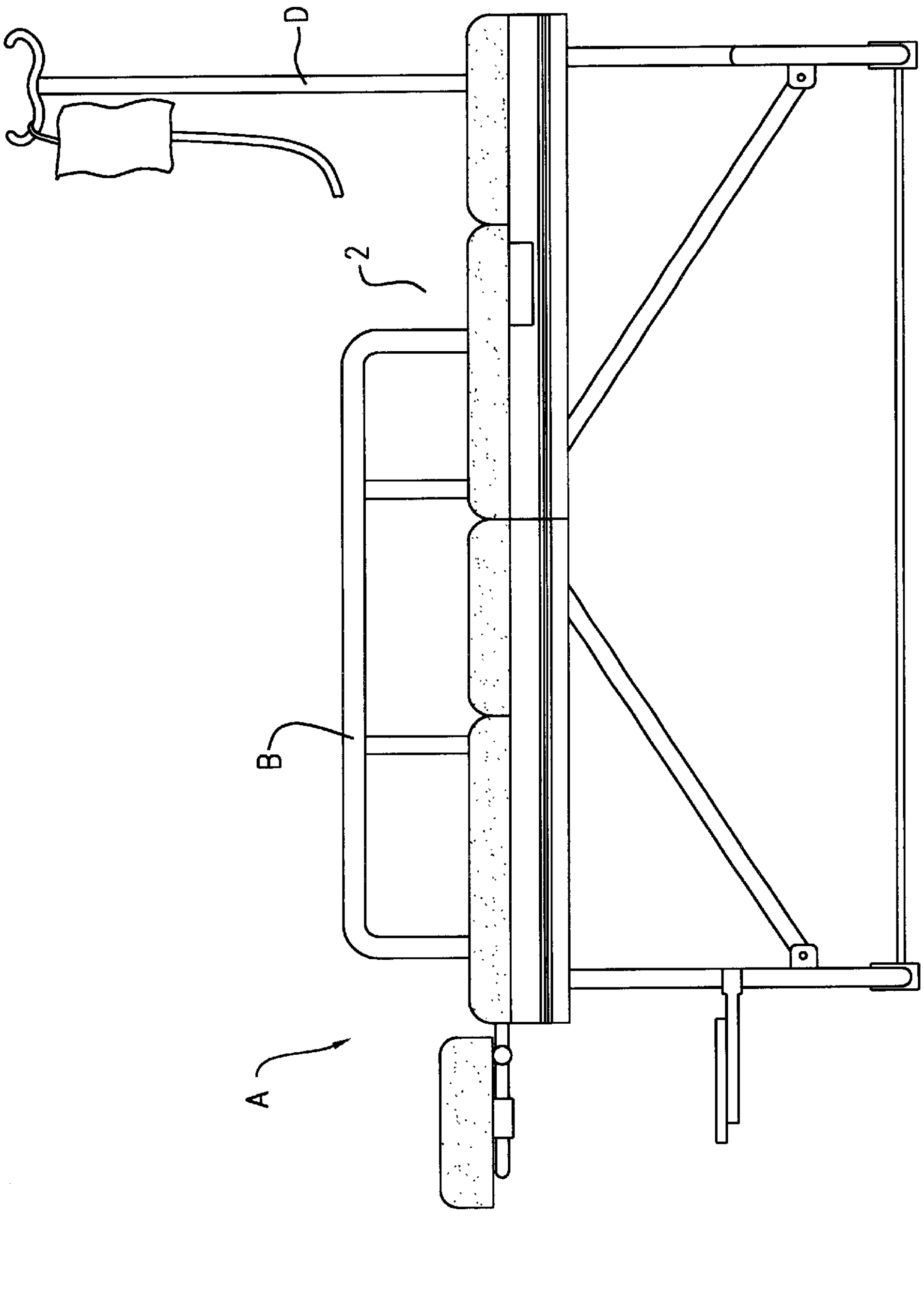
FIG. 12 illustrates another example of use of the massage bed of the invention.

FIG. 12 shows a further example of use of the massage bed of the invention. If a protective fence B and an intravenous injection holder mounting frame D are provided on both sides of the massage bed A, the present invention can serve as a bed for medical use.

In sum, the present invention has the following advantages:

1. The massage bed of the invention can be folded into a case to facilitate transport.

2. The massage bed, when folded, is compact and light to facilitate storage.

3. The massage bed of the invention is provided with an inclination adjusting structure to allow adjustment of the angle of inclination of the back pad to allow the masseur to adjust the sitting or lying posture of the user when massaging the shoulders and neck. The invention is therefore an ergonomic design.

4. The provision of the waist and hip height adjusting structure permits adjustment of the inclination of the waist and hip pad to enable users with injured waists to lie comfortably on the massage bed so that the user's waist pain will not become aggravated due to improper posture.

5. The pillow provides a good support for the user's head, and the height and angle of the pillow can be adjusted to adapt to different users so that the head muscles of the user can relax to thereby enhancing the massaging effect.

6. The rest plate at the lower end of the pillow provides a support for the elbows of the user to help the user relax the shoulder muscles.

7. The foot pad can be pulled outwardly to provide flexible adjustment for users of different heights.

Although the present invention has been illustrated and described with reference to the preferred embodiment thereof, it should be understood that it is in no way limited to the details of such embodiment but is capable of numerous modifications within the scope of the appended claims.

What is claimed is:

1. Massage bed structure comprising a bed frame, a mattress, an inclination adjusting structure and a height adjusting structure to lock said bed frame and said mattress relative to each other, wherein:

said bed frame includes first and second frames, left and right leg frames, a rest plate, and four support rods;

said first frame has a hollow portion in which a first plate is disposed, said first plate having a bottom side with an inverted U-shaped fastener, and an intermediate section provided with a securing plate, said first plate and said securing plate being mounted relative to each other by a connecting link, and a first pivotal edge provided with an inverted U-shaped fastener on an inner side thereof;

said second frame has a hollow portion in which a second plate is disposed, said second plate being provided with two grooves and having a bottom side provided with an inverted U-shaped fastener, and a pivotal edge provided with an inverted U-shaped fastener on an inner side thereof;

said left leg frame has left and right sides each provided with a securing pin and an insert tube, and at least one anti-slip leg sleeve mounted to a bottom portion of said left leg frame;

said right leg frame has left and right sides respectively provided with securing pins, and at least one anti-slip leg sleeve mounted to a bottom portion of the said right leg frame;

said rest plate has one side provided with two insert rods, each of which has a sleeve fitted thereon;

each of said support rods has one end disposed on the respective inverted U-shaped fastener on said pivotal edges of said first and second frames and another end disposed on the respective securing pin of said left and right leg frames;

said mattress includes a back pad, a waist and hip pad, a securing pad, a foot pad and a pillow, said back pad having one side provided with two insert holes for insertion of sleeves, said foot pad having a bottom portion provided with a positioning handle, wherein said pillow has a central portion formed as a hollow, and a bottom portion provided with hook and loop fasteners, an adjusting frame which is substantially U-shaped having insert rods at two ends thereof which have intermediate sections each provided with an adjusting assembly, said adjusting assemblies being formed by two indexing blocks and a handle, said adjusting frame having a bottom portion provided with hook and loop fasteners;

said inclination adjusting structure is provided with an upper arm and a lower arm, said upper arm having one side provided with toothed grooves, said lower arm having a spring disposed therein and being lockably provided with a retaining member, said upper arm being secured to said back pad and said lower arm being secured to said first plate of said first frame; and said waist and hip height adjusting structure includes a seat and a support bar, said seat having an interior provided with a spring and one side provided with a lock pin, said support bar being within said seat interior and having high and low positioning holes on the side corresponding to said lock pin, said seat being secured to said securing plate of said first frame and said support bar being secured to said waist and hip pad;

whereby said massage bed is foldable into a compact configuration to facilitate transport and storage.

2. The massage bed structure as claimed in claim 1, wherein said massage bed structure has two sides respectively provided with a protective fence and an intravenous injection holder mounting frame so as to serve as a bed for medical purposes.

* * * * *